(12) United States Patent
Esat et al.

(10) Patent No.: US 9,044,528 B2
(45) Date of Patent: Jun. 2, 2015

(54) ARTICLE AND METHOD OF SURFACE TREATMENT OF AN ARTICLE

(75) Inventors: Minoo Esat, London (GB); William Bonfield, Herts (GB); Mohan Edirisinghe, Middlesex (GB); Jie Huang, Cambridge (GB); Xiang Li, London (GB)

(73) Assignee: UCL Business PLC, London (GB)

( * ) Notice: Subject to any disclaimer, the term of this patent is extended or adjusted under 35 U.S.C. 154(b) by 608 days.

(21) Appl. No.: 13/131,919

(22) PCT Filed: Nov. 30, 2009

(86) PCT No.: PCT/GB2009/002788
§ 371 (c)(1),
(2), (4) Date: Aug. 19, 2011

(87) PCT Pub. No.: WO2010/063993
PCT Pub. Date: Jun. 10, 2010

(65) Prior Publication Data
US 2012/0064290 A1    Mar. 15, 2012

(30) Foreign Application Priority Data
Dec. 1, 2008    (GB) .................................. 0821927.1

(51) Int. Cl.
| | |
|---|---|
| B32B 3/24 | (2006.01) |
| B32B 5/00 | (2006.01) |
| B32B 17/06 | (2006.01) |
| B32B 18/00 | (2006.01) |
| B32B 15/04 | (2006.01) |
| B32B 3/30 | (2006.01) |
| A61L 27/32 | (2006.01) |
| A61L 27/50 | (2006.01) |
| A61F 2/28 | (2006.01) |

(Continued)

(52) U.S. Cl.
CPC ............. *A61L 27/04* (2013.01); *A61F 2/30767* (2013.01); *A61F 2310/00011* (2013.01); *A61F 2/3094* (2013.01); *A61F 2310/00796* (2013.01); *A61F 2002/3093* (2013.01); *A61F 2002/30929* (2013.01); *A61L 27/06* (2013.01); *A61L 27/306* (2013.01); *A61L 27/32* (2013.01); *A61L 27/34* (2013.01)

(58) Field of Classification Search
None
See application file for complete search history.

(56) References Cited

U.S. PATENT DOCUMENTS 3,905,777 A * 9/1975 Lacroix .......................... 428/550
4,103,002 A * 7/1978 Hench et al. ................... 428/155
(Continued)

FOREIGN PATENT DOCUMENTS

| CN | 1184626 A | 6/1998 | |
|---|---|---|---|
| GB | 2397233 A * | 7/2004 | .............. A61L 27/28 |

(Continued)

OTHER PUBLICATIONS

First Office Action issued in CN Application No. 200980148248.X, May 14, 2013.
(Continued)

*Primary Examiner* — Jeff Vonch
(74) *Attorney, Agent, or Firm* — Bell & Manning, LLC

(57) ABSTRACT

An article comprising: a substrate; and over at least part of a surface of said substrate an outer coating of hydroxyapatite and an intermediate bonding layer bonded to said substrate and to said outer coating, wherein a mechanical interlock is present between said substrate and said outer coating.

19 Claims, 5 Drawing Sheets

(51) Int. Cl.
*A61L 27/04* (2006.01)
*A61F 2/30* (2006.01)
*A61L 27/06* (2006.01)
*A61L 27/30* (2006.01)
*A61L 27/34* (2006.01)

(56) References Cited

U.S. PATENT DOCUMENTS

| | | | | |
|---|---|---|---|---|
| 4,483,678 | A * | 11/1984 | Nishio et al. | 433/201.1 |
| 4,491,987 | A * | 1/1985 | Park | 623/23.59 |
| 4,542,539 | A * | 9/1985 | Rowe et al. | 623/23.57 |
| 4,550,448 | A * | 11/1985 | Kenna | 623/23.6 |
| 4,990,163 | A * | 2/1991 | Ducheyne et al. | 427/2.24 |
| 5,104,410 | A * | 4/1992 | Chowdhary | 623/11.11 |
| 5,263,986 | A * | 11/1993 | Noiles et al. | 623/23.55 |
| 5,314,475 | A | 5/1994 | Repenning | |
| 5,480,438 | A * | 1/1996 | Arima et al. | 623/23.6 |
| 5,549,704 | A * | 8/1996 | Sutter | 623/23.13 |
| 5,645,593 | A * | 7/1997 | Woods et al. | 623/23.5 |
| 5,868,796 | A | 2/1999 | Buechel et al. | |
| 6,008,432 | A | 12/1999 | Taylor | |
| 6,261,322 | B1 * | 7/2001 | Despres et al. | 623/23.53 |
| 6,534,197 | B2 * | 3/2003 | Noda et al. | 428/689 |
| 6,805,898 | B1 * | 10/2004 | Wu et al. | 427/2.25 |
| 6,984,236 | B2 * | 1/2006 | Raab | 606/76 |
| 7,157,096 | B2 * | 1/2007 | Zhang et al. | 424/422 |
| 7,501,073 | B2 * | 3/2009 | Wen et al. | 216/109 |
| 7,531,120 | B2 * | 5/2009 | Van Rijn et al. | 264/299 |
| 7,569,285 | B2 * | 8/2009 | Schwartz et al. | 428/629 |
| 7,901,727 | B2 * | 3/2011 | Hofmann et al. | 427/2.1 |
| 8,070,797 | B2 * | 12/2011 | Flanagan et al. | 623/1.42 |
| 8,323,348 | B2 * | 12/2012 | Lai et al. | 623/23.5 |
| 8,415,019 | B2 * | 4/2013 | Pawar et al. | 428/469 |
| 2001/0039454 | A1 * | 11/2001 | Ricci et al. | 623/23.5 |
| 2002/0018851 | A1 | 2/2002 | Chang et al. | |
| 2003/0045941 | A1 * | 3/2003 | Lewallen | 623/20.17 |
| 2003/0108658 | A1 * | 6/2003 | Andersch et al. | 427/2.1 |
| 2004/0167633 | A1 * | 8/2004 | Wen et al. | 623/23.57 |
| 2005/0113934 | A1 | 5/2005 | Kim et al. | |
| 2005/0161120 | A1 * | 7/2005 | Inagaki et al. | 148/220 |
| 2006/0100716 | A1 * | 5/2006 | Lerf | 623/23.5 |
| 2006/0271203 | A1 * | 11/2006 | Hermansson | 623/23.51 |
| 2007/0078521 | A1 * | 4/2007 | Overholser et al. | 623/23.53 |
| 2007/0116734 | A1 * | 5/2007 | Akash | 424/423 |
| 2007/0142914 | A1 * | 6/2007 | Jones et al. | 623/14.13 |
| 2007/0173952 | A1 * | 7/2007 | Hermansson et al. | 623/23.76 |
| 2007/0244548 | A1 * | 10/2007 | Myers et al. | 623/1.42 |
| 2008/0091209 | A1 | 4/2008 | Schmotzer et al. | |
| 2008/0274160 | A1 * | 11/2008 | Kashiwabara et al. | 424/423 |
| 2009/0011117 | A1 * | 1/2009 | Nunez et al. | 427/2.31 |
| 2009/0018639 | A1 * | 1/2009 | Kuehling | 623/1.15 |
| 2009/0082865 | A1 * | 3/2009 | Raja et al. | 623/16.11 |
| 2009/0138077 | A1 * | 5/2009 | Weber et al. | 623/1.46 |
| 2009/0259300 | A1 * | 10/2009 | Dorogy et al. | 623/1.36 |
| 2010/0057197 | A1 * | 3/2010 | Weber et al. | 623/1.42 |
| 2010/0303722 | A1 * | 12/2010 | Jin et al. | 424/9.1 |
| 2011/0143127 | A1 * | 6/2011 | Gupta et al. | 428/336 |
| 2012/0035739 | A1 * | 2/2012 | Wilhemsson et al. | 623/23.53 |
| 2014/0044861 | A1 * | 2/2014 | Boey et al. | 427/2.24 |

FOREIGN PATENT DOCUMENTS

| | | | | |
|---|---|---|---|---|
| JP | 03218769 | A * | 9/1991 | A61L 27/00 |
| JP | 04242659 | A | 8/1992 | |
| JP | 2007061544 | A * | 3/2007 | |
| WO | WO 86/06617 | A1 | 11/1986 | |
| WO | WO 2004/103423 | A1 | 12/2004 | |

OTHER PUBLICATIONS

GB Search Report received in GB0821927.1, Mar. 31, 2009.
International Search Report and Written Opinion received in PCT/GB2009/002788, Oct. 21, 2010.
Li et al., Novel patterning of nano-bioceramics: template-assisted electrohydrodynamic atomization spraying, Journal of the Royal Society Interface Royal Society UK, vol. 5, No. 19, Feb. 6, 2008, pp. 253-257.
Curtis et al., Topographical control of cells, Biomaterials, vol. 18, 1997, pp. 1573-1583.
Huang et al., In vitro assessment of the biological response to nano-sized hydroxyapatite, Journal of Materials Science: Materials in Medicine, vol. 15, 2004, pp. 441-445.
Huang, Electrospraying of a nano-hydroxyapatite suspension, Journal of Materials Science, vol. 39, 2004, pp. 1029-1032.
Mahalingam, Characteristics of electrohydrodynamically prepared titanium dioxide films, Applied Physics A, Materials Science & Processing, vol. 89, Aug. 28, 2007, pp. 987-993.

* cited by examiner

etc.

ARTICLE AND METHOD OF SURFACE TREATMENT OF AN ARTICLE

The present invention relates to coatings on articles including prosthetic devices, in particular coatings on orthopedic implants.

With an ageing population worldwide, there is an increasing demand for biomedical implants. In the U.K., there were 43,000 hip replacement carried out in 2003 (UK national audit office report 2003) bringing mobility and relief from pain for patients, and it is believed that this figure will keep on rising in the future.

The use of biomedical inserts is also increasing. Inserts may be articles placed inside the human body temporarily. For example, catheters and stents are inserts.

The present application relates to inserts or implants for use in the human or animal body, particularly to biomaterial coatings on such inserts or implants. A biomaterial is a material which is compatible with human tissue. That is, a material which is not rejected by the human body. Biomaterials may be ceramics, metals, polymers or a combination of such materials. One particular biomaterial which has attracted interest is hydroxyapatite (HA).

In the healthcare industry, hydroxyapatite (HA) has been widely used as a coating material to combine its sound biological properties and excellent mechanical properties of traditional metallic implant materials. HA is present as 60-70% of the mineral of natural bone tissue. It is osteoconductive as it can promote direct bonding with bone tissue.

There are various coating techniques for HA including plasma spraying, dip coating, sputtering and pulsed laser deposition and more recently electrostatic atomization spray deposition has been utilized. Plasma spraying is the most commercially used method for producing HA coatings; the thickness of the coatings varies from 30 to 200 μm. However, process control is quite complicated. The high processing temperatures encountered by HA induce some decomposition to soluble calcium phosphate compounds. Also, the rapid cooling generates amorphous coatings. The dip coating technique is useful to prepare HA coatings with a thickness between 0.05-0.5 mm. It is a cheap and fast technique and also capable of producing coatings on substrates of complex shapes, but dip coating requires high sintering temperatures, which cause HA dehydroxylation. Sputter coating and pulsed laser deposition techniques are capable of producing a uniform coating thickness on flat substrates; the thickness can be controlled between 0.02 μm and 5 μm. However, the thin coatings made using this method are relatively expensive and are largely amorphous. Both sputter coating and pulsed laser deposition are not capable of producing coatings onto substrates of complex geometries.

It is desirable to provide an article with a coating of hydroxyapatite which is well adhered to the surface of the substrate. In particular, it is desirable to provide a method in which complex geometries can be covered.

The present invention provides an insert or implant comprising: a substrate; and over at least part of a surface of said substrate an outer coating of a biomaterial and an intermediate bonding layer bonded to said substrate and to said outer coating, wherein a mechanical interlock is present between said substrate and said outer coating.

The present invention further provides a method of surface treatment of at least part of a surface of an insert or implant, said method comprising: depositing an intermediate bonding layer and an outer coating of a biomaterial on at least part of the surface of the insert or implant such that said intermediate bonding layer is bonded to said substrate and to said outer coating and a mechanical interlock is present between said intermediate bonding layer and said outer coating.

Embodiments of the invention will now be described, by way of example only, with reference to the accompanying drawings in which.

Figure 1:
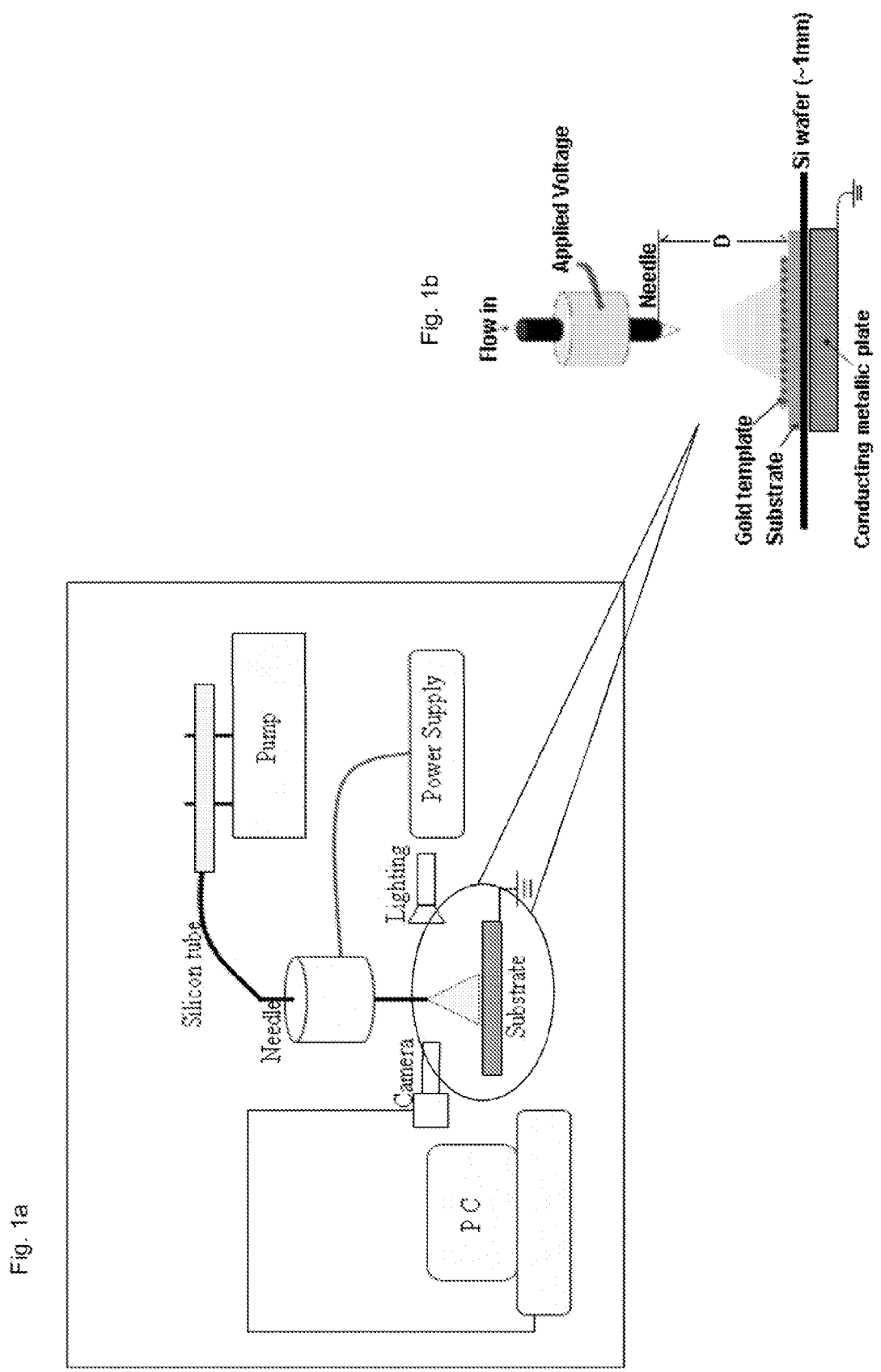
FIG. 1a is a schematic illustration of the template-assisted electrohydrodynamic atomization (TAEA) spraying method used in the present invention.
FIG. 1b illustrates the ground electrode configuration used during the (TAEA) process of the present invention.

Examples of the present invention below relate to the biomaterial being hydroxyapatite (HA). However, other biomaterials are equally applicable to the present application. Biomaterials are materials suitable for being implanted into the human body. That is, they are not detrimental to the human when they are placed in the human body. Biomaterials include: Polymers: Polymethacrylic acid (PMMA), Polyethylene (PE), Plydimethylsulphoxide (PDMS), Polypropylene (PP), Polysulphone (PS), Polycarbonate (PC), Polyglycolic acid (PGA), Polylactic acid (PLA), Polycaprolactone (PCL), Polydioxanone (PDS), Polyhydroxybutyrate (PHB), Polyorthoester, Poly(2-hydroxy-ethyl-methacrylate) (PHEMA). Bioceramics: Hydroxyapatite (HA), Amorphous Phase (ACP), Alpha tricalcium phosphate (a-TCP), Beta tricalcium phosphate (B-TCP), Tetracalcium phosphate (TTCP), Oxyhydroxyapatite (OHA), substituted calcium phosphates, bioactive glasses and bioactive glass-ceramics (Details in: Hench L. L., 1998, 'Bioceramics', J. Am. Ceram. Soc. 81, 1705-28).

Composite biomaterials may also be used. These include ceramic-metal, ceramic-ceramic, ceramic-polymer and metal-polymer composites. The present invention is not limited to the specific type of biomaterial forming the outer coating.

Electrohydrodynamic atomization (EHDA) is a simple, economical process that is capable of producing a uniform coating with a good morphology. This technique has been applied to deposit calcium phosphate coatings on metallic substrates. The process consists of a grounded electrode and a nozzle (needle), which is connected to a high voltage supply. The liquid or ceramic suspension is fed to the nozzle by a pump at a controlled flow rate. The flowing medium is subjected to an electrical field, which is generated by the applied voltage between the nozzle and ground electrode, and generates an elongated jet, which subsequently detaches from the body of liquid and disintegrates into droplets. The jet and droplet generation are classified into different modes of spraying governed by the geometry of jetting. Out of several different modes, the cone-jet mode, which is the steadiest mode of spraying, regularizes the break-up of jet to generate fine and uniform droplets of a few micrometers in size. The droplets travel from needle tip to the targeted substrate to therefore form deposition. More can be found about EDHA from the following articles: (1) S. C. G Leeuwenburgh, J. G. C Wolke, J. Schoonman and J. A. Jansen (2003) Electrostatic spray deposition (ESD) of calcium phosphate coatings. Biomed. Mater. Res. A 66A, 330-334; (2) A. Jaworek and A. Krupa (1996) Generation and characteristics of the precession mode of EHD spraying. J. Aerosol. Sci. 27, 75-82; (3) A. Jaworek and A. Krupa (1999) Classification of the modes of EHD spraying. J. Aerosol. Sci. 30, 873-893.

Studies have been carried out on processing 3-D surface structures, which is known to affect initial biological response, on the substance surfaces for biomedical applications. The techniques, such as etching, ink jet printing and electrohydrodynamic 3-D printing, have been widely utilized to create the 3-D biomaterials. However, such techniques are either limited for the material's physical properties, or technically cumbersome. For instance, etching is normally used to create an ordered surface structure on relatively ductile materials, such as polymeric and metallic materials. It is difficult to use it for brittle and chemically stable ceramics, such as HA. At present, it is still difficult to use printing techniques to create a precise small dimensional surface structure. The 3-D patterns printed are normally of a few hundred micrometers, which is too high a magnitude compared to the osteoblast dimension (~40 μm). Thus, more recently, based on the study of EHDA spraying, a novel patterning technique, called template-assisted electrohydrodynamic atomisation (TAEA) spraying, was developed and used for nHA patterning process. More information about TAEA can be found in an article by X. Li, J. Huang and M. J. Edirisinghe (2007) Novel patterning of nano-bioceramics: template-assisted electrohydrodynamic atomization spraying. J. Royal. Soc. Interface. 5, 253-257.

Both EHDA and TAEA techniques offer a range of advantages, such as easy control of coverage of a large uniform area, low cost, simple setup; compatibility with micro-fabrication technology and suitability for industrial production. The interfacial stability is crucial to the material's mechanical properties.

To enhance a composite material's properties, mechanical interlocking can be induced to improve the bonding and therefore the stability at the interface between two different substances. Creating surface texture is an effective way to achieve a mechanical interlocking at the interface. Roughening may be achieved by grit blasting or wet etching techniques in which corrosion pits are formed by application of strong acids for short periods of time. However, a number of drawbacks have been found. The surfaces present random morphology, which may weaken the enhancement of adhesion of upper layers. Also, the wet-etching techniques may lead to substrate corrosion during clinical practices due to the undesirable ions left during the roughening process. Furthermore, it is difficult to control the substrate surface topography during industrial scale manufacturing. A number of investigations have demonstrated that the significantly improved bonding of coatings could be achieved via roughening the substrate surface before coating process. Some studies showed that the bonding of the HA coatings can also be enhanced by inducing a chemistry bonding. A continuous $TiO_2$ buffer layer pre coated on a Ti substrate was found significantly to enhance HA/Ti interfacial adhesion and therefore improve HA mechanical stability during the clinical practices.

In the present invention we combine these two bonding enhancement concepts. The substrates are patterned with an intermediate bonding layer to change the surface texture, and subsequently coated with HA. This new intermediate bonding layer is interlocked with the HA coating on a substrate. Thus, both the mechanical interlocking and chemistry bonding improve implant material's functional performance for clinical practices (i.e. improve bonding). Chemistry bonding may include traction or Van der Waals forces. A mechanical interlock may also be present between the substrate and the intermediate layer. For example, the substrate may be roughened prior to application of the intermediate bonding layer. Therefore, the intermediate bonding layer is bonded to the substrate. That bond may be a chemical bond and/or a mechanical interlock bond.

The substrate may be Ti, Ti alloy, stainless steel (preferably 316L), Co—Cr—Mo alloys etc. The substrate is patterned with an intermediate bonding layer which desirably comprises $TiO_2$, $ZrO_2$ (Zirconium), calcium titanate or other complex salts, such as $Fe_2O_3$, or a composite of the materials of the substrate and the outer layer. The intermediate bonding layer has a non-planar surface topography prior to the deposition of the outer coating of hydroxyapatite. That is, the intermediate bonding layer has a pattern on it with, in plan, first regions which are relatively thick and second regions which are relatively thin.

The intermediate bonding layers may be applied by projecting droplets of material onto the substrate. A potential difference may be used to attract the droplets onto the substrate. The intermediate bonding layer can be patterned in any way. For example, the intermediate bonding layer could be deposited and then patterned by etching of the substantially planar layer, ink jet printing the intermediate bonding layer or electrohydrodynamically 3-D printing the intermediate bonding layer. Desirably the intermediate bonding layer is applied using TAEA. This allows precise control of the surface topography of the intermediate layer addressing at least some of the disadvantages of prior art ways of providing surface texture. In this method the intermediate bonding layer is applied by projecting droplets of material through a template. A potential difference is used to attract the droplets onto the substrate through the template.

The intermediate bonding layer desirably has a bond strength between it and the substrate and/or between it and the hydroxyapatite which is larger than a bond strength between the substrate and the hydroxyapatite. In this way the presence of the intermediate bonding layer results in a better chemical bond of the hydroxyapatite to the substrate.

The hydroxyapatite may be applied in any way, in particular in droplet form. It is preferred to use EHDA to apply the hydroxyapatite. In this process a potential difference is used to attract droplets of material onto the substrate.

In one embodiment the intermediate bonding layer has through holes in it such that the outer coating is in contact with the substrate as well as with the intermediate bonding layer. In one embodiment the intermediate bonding layer has a minimum thickness which varies from 0-10 μm. That is, the second regions vary from being non existent (being 0 μm thick up to having a thickness of up to 10 μm). In the case of a titanium substrate, for example, a natural layer of $TiO_2$ may be present of about 125 nm thickness. Thus a preferred minimum thickness is between 125 nm or 200 nm and 10 μm. In one embodiment the intermediate bonding layer has a maximum thickness (e.g. the thickness of the first regions) of 0.2-30 μm, preferably 0.5-20 μm. Thus, the first regions are relatively thick and second regions are relatively thin compared to one another. The difference in thickness of the intermediate layer between the first and second regions is between 0.2 and 30 μm. It has been found that this difference in thickness provides sufficient mechanical interlock; even a 200 nm difference in thickness can help in bonding. By contrast, the outer coating, although it follows the topography of the intermediate coating, varies in thickness by only 0-5 µm. The thickness of the outer layer is between 0.1-100 µm, preferably 0.5-50 µm. The total thickness of all layers is in the range of 0.1-200 µm, preferably 0.5-50 µm, more preferably 1-25 µm. This can be achievable by using EHDA.

The pattern of the intermediate bonding layer is not important so long as it provides the desired mechanical interlock. It may be desirable, for ease of manufacture, to provide a substantially regular pattern (in plan) in which first and second regions which are of different heights. For example, the regular pattern may be a series of squares or other shapes which close pack (e.g. hexagons or triangles). In another embodiment the pattern comprises a plurality of parallel lines. In another embodiment there may be circular shapes in plan. Different patterns may result in better interlocking. A contact guiding pattern may be preferable. A contact guiding pattern is a pattern which results in cellular orientation when the implant or insert is in the human or animal body. Cellular orientation has been found to be beneficial for growth of cells for good bonding of cells to an implant or insert. For example, if contact guiding patterns are used on bone implants, this can desirably lead to sculpturing of the bone. Adam Curtis et al. in Biomaterials 18 (1997) 1573-1583 describes contact guiding phenomenon in detail. A contact guiding pattern may comprise any of the above mentioned specific shapes.

Desirably adjacent first regions are between 5 and 80 µm apart (center to center). In one embodiment adjacent second regions are between 5 and 100 µm apart (center to center).

Detailed examples of embodiments of the present invention are given below.

EXPERIMENTAL PROCEDURE

1. Materials
1.1 $TiO_2$ So/Titanium (IV) isopropoxide, $Ti[OCH(CH_3)_2]_4$ (Sigma-Aldrich, Poole, UK) was used as a precursor. The titania sol was prepared by transferring 2 wt % of precursor to an air tight bottle containing ethanol and the resulting solution was stirred using a magnetic stirrer for 3 hours at ambient conditions. The air tight bottles were used in order to prevent any evaporation or contamination until they were used. The sol obtained using ~2 wt % of precursor was very stable and no sedimentation occurred on standing indefinitely.

1.2 HA Suspension

HA was synthesised based on a wet precipitation reaction between calcium hydroxide and orthophosphoric acid, both obtained from BDH, UK. 0.3M orthophosphoic acid was added drop wise to 0.5M calcium hydroxide solution under continuous stirring at room temperature, while the pH was kept above 10.5 by the addition of ammonia solution. The precipitates obtained were further aged for two weeks and then washed with boiling water. The aged nHA particles were taken up in ethanol to prepare a 6 wt % suspension suitable for electrohydrodynamic flow process. Further details of suspension preparation and characterisation of the HA particles and suspension are described elsewhere (e.g. Huang et al. Journal of Materials Science 39 (2004) 1029-1032 and Huang et al. Journal of Material Science: Materials in Medicine 15 (2004) 441-445).

2. $TiO_2$ Patterning Process Using TAEA

The TAEA equipment layout used in this work is illustrated in FIG. 1a. The stainless steel needle used had an inner diameter of ~300 µm. Freshly prepared $TiO_2$ sol was syringed to the needle at flow rates of 10 µl/min with the applied voltage between the needle and the ground electrode varied up to 6 kV to investigate electrohydrodynamic spraying scenarios. As shown in FIG. 1b, a specifically designed ground electrode configuration was used during the TAEA process. A silicon wafer was placed on top of the actual Ti substrate. The distance between the stainless steel needle and substrate was fixed at 40 mm. Commercially pure titanium substrate plates were polished using P4000 silicon carbide grinding paper, and subsequently cleaned using acetone and ethanol. The spraying time was controlled at 60 seconds. A range of templates with different geometries were used to mask the Ti substrate during patterning.

3. HA Coating Process Using EHDA

The EHDA spraying equipment setup lay out for the HA coating process is similar to the previous TAEA spraying (FIG. 1a). The only difference is the ground electrode configuration. Instead of being covered with a silicon wafer, the $TiO_2$ patterned Ti substrate was directly earthed. The freshly prepared 6% wt HA suspension was feed into the needle at the flow rate of 20 µl/min. The substrate-needle distance was set at 40 mm too. The applied voltage was varied up to 6 kV to achieve the stable cone jet mode. The HA spraying time was controlled at 60 seconds.

4. Characterization

The morphology of $TiO_2$ patterns and $TiO_2$ interlocked HA coatings were examined using optical microscopy and field emission scanning electron microscopy (SEM, JEOLJSM/6301F) to understand the microstructure. For SEM, the working distance was 15 mm and the accelerating voltage was set at 15 kV. The preliminary cell culture using human osteoblast (HOB) was also carried out to characterize the bioactivity of the lineshaped $TiO_2$ interlocked HA coating. The visualisation of the HOB cell orientation was carried out using a Leica SPII confocal microscope equipped with a LED Diode laser to excite the Hoechst 33258 fluorophore at 405 nm.

Results

Figure 2:
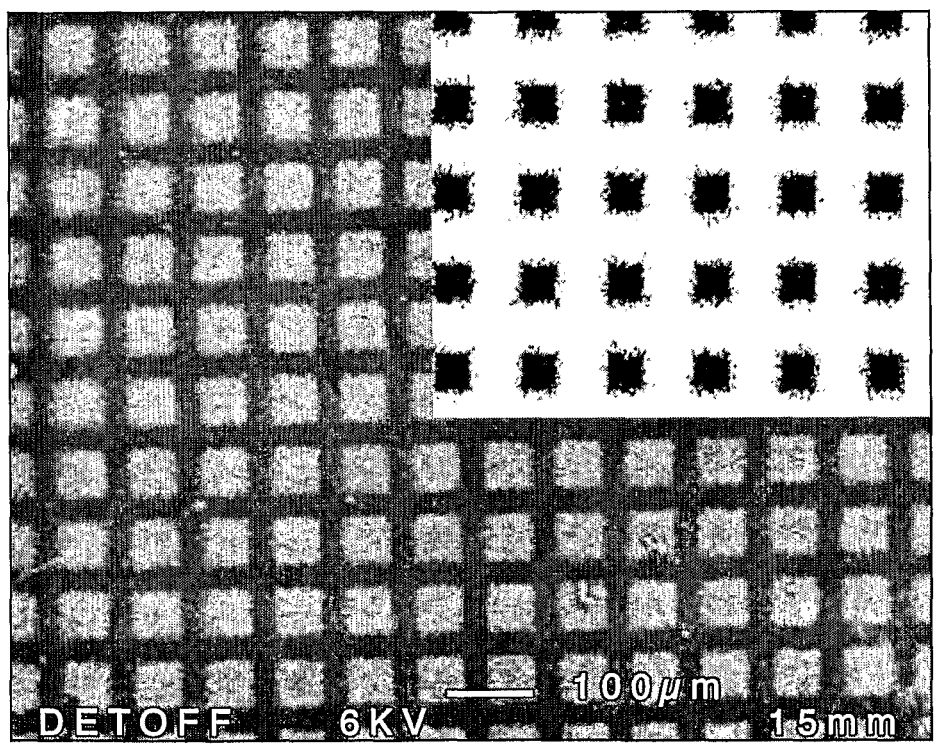
FIG. 2 is an SEM micrograph of a substrate surface which has had one embodiment of intermediate bonding coating applied.
Figure 3:
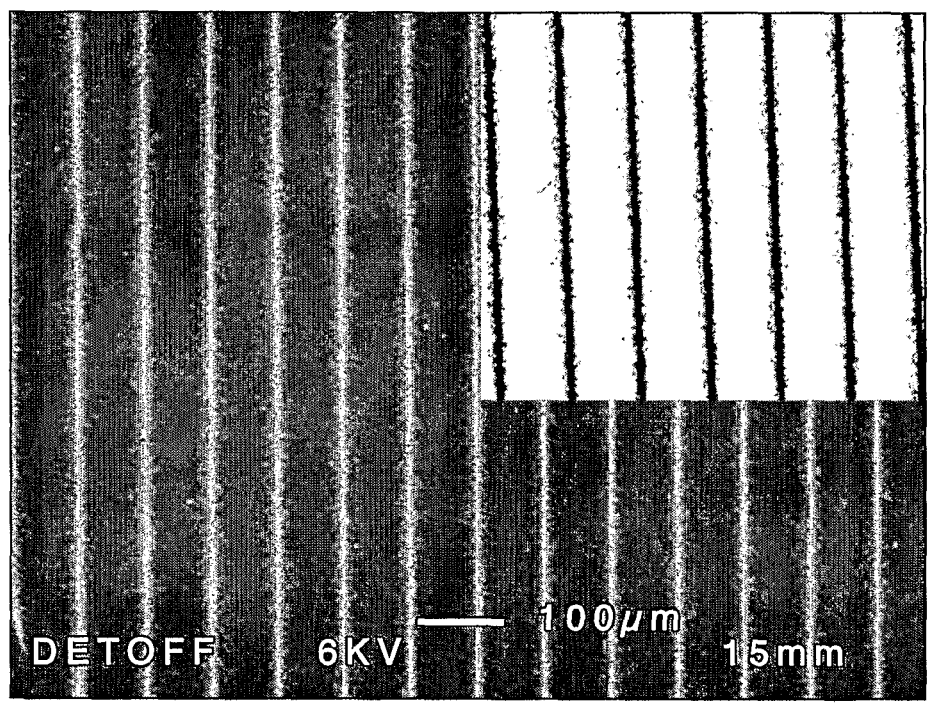
FIG. 3 is an SEM micrograph of a substrate surface which has had another embodiment of intermediate bonding layer applied.
Figure 4A:
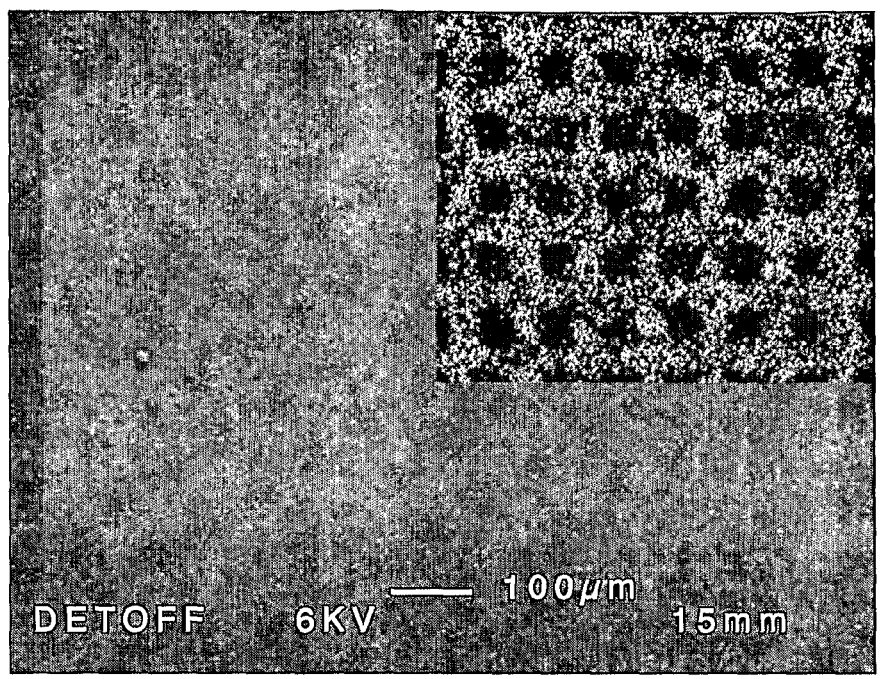
FIG. 4a is an SEM micrograph of the outer coating applied to an intermediate layer with the configuration of FIG. 2.
Figure 4B:
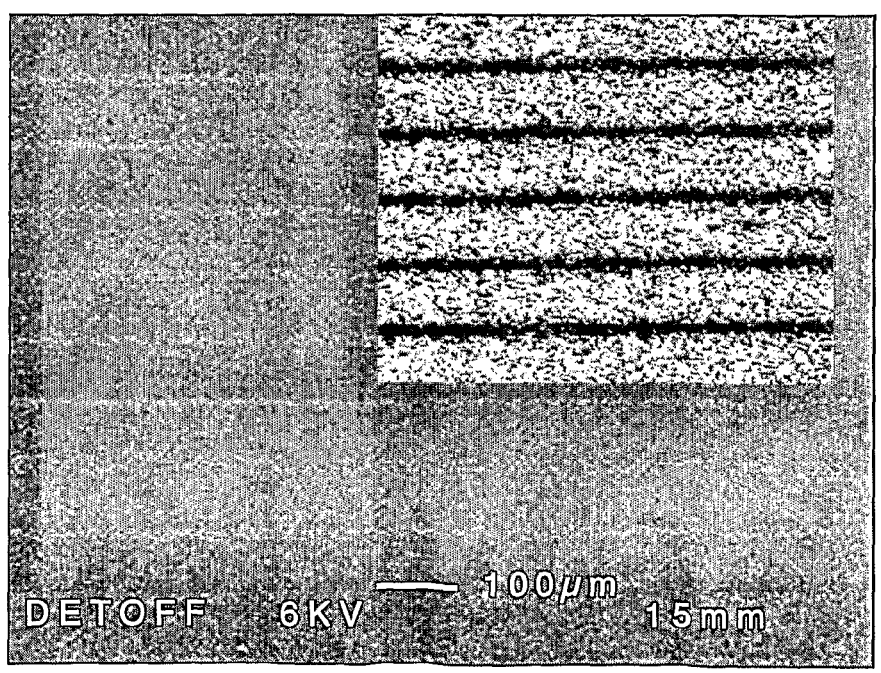
FIG. 4b is a SEM micrograph of the outer coating applied to an intermediate layer with the configuration of FIG. 3.
Figure 5A:
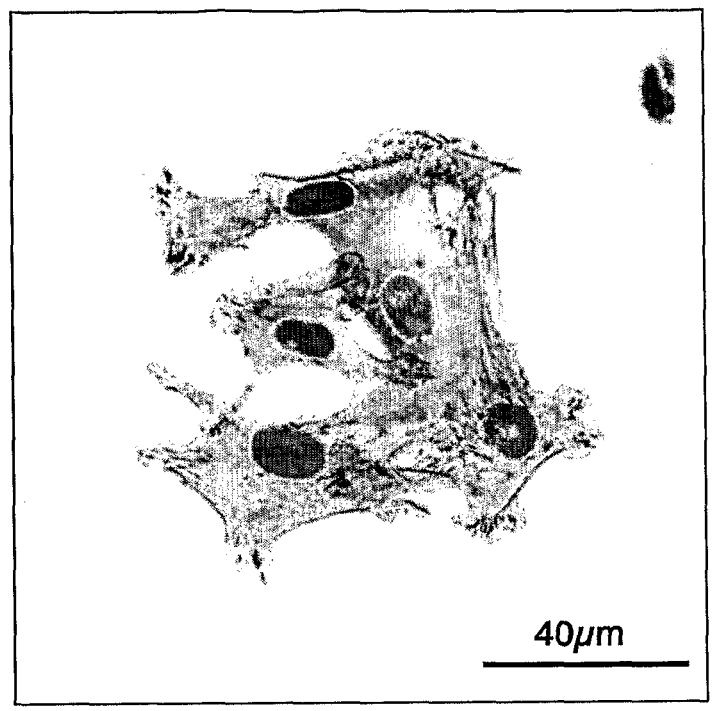
FIG. 5a is an SEM micrograph showing that the outer coating of hydroxyapatite of the present invention provides favourable binding sites for human osteoblast (HOB)
Figure 5B:
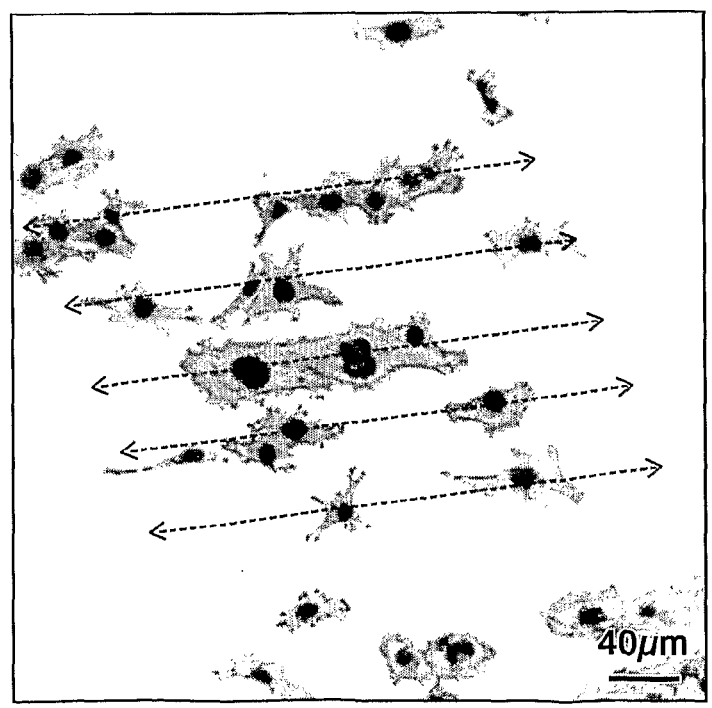
FIG. 5b is an SEM micrograph which shows that the human osteoblast aligns in a specific direction on a coating of the present invention.

As shown in FIG. 2, by using a square template $TiO_2$ particles distributed into squareshaped islands on the Ti surface was prepared. The width of the islands was controlled at 42 µm with the standard deviation of 4 µm, and the spaces between the islands are 48 µm with the standard deviation of 4 µm. By using parallel templates on a polished titanium substrate, the line shape $TiO_2$ patterns were also prepared on the Ti substrate as shown in FIG. 3. The line width is 13 µm with the standard deviation of 3 µm, and the spacing between the lines is 65 µm with the standard deviation of 3 µm. All $TiO_2$ patterns prepared exhibit uniform and ordered topography. The spaces between the islands were kept constant and varied only by a few micrometers, and by using the same template and the same process parameters, the shape and size of islands in the entire coating was kept the same. After TAEA patterning process, the subsequent EHDA spraying process was carried out to prepare the bioactive HA layer on the interlocking layers. As shown in FIGS. 4a and 4b, the entire HA coating presents uniform and continuous topography, and from the optical microscopy image, it is clearly shown that the square and line shaped 'hills' distribute orderly in the HA coating. The preliminary in-vitro study was carried out to characterize the bioactivity of this novel HA coating with line-shaped interlocking layer. The fluorescent confocal microscopy image showing the differentially stained nuclei and cytoskeletal structures of HOB cells cultured on the surfaces prepared are shown in FIG. 5. In FIG. 5a, the image of higher magnification shows that the HA surface provides favorable binding sites for the HOB cells attachment. Numerous binding domains of the HOB cells were observed. This was a positive indication that the newly prepared HA coating support the HOB cell attachment and adhesion. Furthermore, as shown in FIG. 5b, instead of the random distribution, the HOB cells align to a specific direction. This phenomenon indicates that the HA coatings with interlocking layer are able to support the cellular attachment, and furthermore guide cellular orientation due to their specific surface topography.

The invention claimed is:

1. An insert or implant comprising:
a substrate; and
over at least part of a surface of said substrate an outer coating of a biomaterial and an intermediate bonding layer bonded to said substrate and to said outer coating, wherein a mechanical interlock is present between said intermediate bonding layer and said outer coating, wherein said intermediate bonding layer has, in plan, first regions which are relatively thick and second regions which are relatively thin, wherein said first and second regions form, in plan, a substantially regular pattern and wherein the outer coating with intermediate bonding layer is able to support cellular attachment,
wherein adjacent first regions are between 5 µm and 80 µm apart,
wherein said intermediate bonding layer comprises $TiO_2$, $ZrO_2$, calcium titanate, a complex salt, $Fe_2O_3$, or a composite of the materials of the substrate and the outer coating,
wherein the biomaterial comprises hydroxyapatite,
and further wherein said intermediate bonding layer has through holes in it such that said outer coating is in contact with said substrate as well as said intermediate bonding layer.

2. The insert or implant of claim 1, wherein a material of said intermediate bonding layer has a bond strength to said substrate which is greater than the bond strength of the material of the outer coating to said substrate.

3. The insert or implant of claim 1, wherein a material of said intermediate bonding layer has a bond strength to said outer coating which is greater than the bond strength of the material of the outer coating to said substrate.

4. The insert or implant of claim 1, wherein said intermediate bonding layer has a minimum thickness of between 0 and 10 µm.

5. The insert or implant of claim 1, wherein said intermediate bonding layer has a maximum thickness of between 0.2 and 30 µm.

6. The insert or implant of claim 1, wherein the difference in thickness between the first and second regions is between 0.2 and 30 µm.

7. The insert or implant of claim 1, wherein said first and second regions form a contact guiding pattern.

8. The insert or implant of claim 1, wherein said first regions are, in plan, in the shape of a triangle, a square, a circle, a hexagon or an octagon or a combination thereof.

9. The insert or implant of claim 1, wherein adjacent second regions are between 5 µm and 100 µm apart.

10. The insert or implant of claim 1, wherein a variation in thickness of the outer coating is in the range of 0-5 µm.

11. The insert or implant of claim 1, wherein said substrate is Ti, a Ti alloy, a stainless steel or a Co—Cr—Mo alloy.

12. An insert or implant comprising:
a substrate; and
over at least part of a surface of said substrate an outer coating of a biomaterial and an intermediate bonding layer bonded to said substrate and to said outer coating, wherein a mechanical interlock is present between said intermediate bonding layer and said outer coating, wherein said intermediate bonding layer has, in plan, first regions which are relatively thick and second regions which are relatively thin, wherein said first and second regions form, in plan, a substantially regular pattern and wherein the outer coating with intermediate bonding layer is able to support cellular attachment,
wherein adjacent second regions are between 5 µm and 100 µm apart,
wherein said intermediate bonding layer comprises $TiO_2$, $ZrO_2$, calcium titanate, a complex salt, $Fe_2O_3$, or a composite of the materials of the substrate and the outer coating,
wherein the biomaterial comprises hydroxyapatite,
and further wherein said intermediate bonding layer has through holes in it such that said outer coating is in contact with said substrate as well as said intermediate bonding layer.

13. The insert or implant of claim 1, wherein the pattern formed by said first and second regions is non-random.

14. The insert or implant of claim 1, wherein adjacent first regions are between 5 µm and 80 µm apart as measured center to center.

15. The insert or implant of claim 12, wherein the pattern formed by said first and second regions is non-random.

16. An insert or implant comprising:
a substrate; and
over at least part of a surface of said substrate an outer coating of a biomaterial and an intermediate bonding layer bonded to said substrate and to said outer coating, wherein a mechanical interlock is present between said intermediate bonding layer and said outer coating, wherein said intermediate bonding layer has, in plan, first regions which are relatively thick and second regions which are relatively thin, wherein said first and second regions form, in plan, a substantially regular pattern and wherein the outer coating with intermediate bonding layer is able to support cellular attachment,
wherein the pattern formed by said first and second regions is non-random,
wherein said intermediate bonding layer comprises $TiO_2$, $ZrO_2$, calcium titanate, a complex salt, $Fe_2O_3$, or a composite of the materials of the substrate and the outer coating,
wherein the biomaterial comprises hydroxyapatite,
and further wherein said intermediate bonding layer has through holes in it such that said outer coating is in contact with said substrate as well as said intermediate bonding layer.

17. The insert or implant of claim 16, wherein said first regions are, in plan, in the shape of a triangle, a square, a circle, a hexagon or an octagon or a combination thereof.

18. The insert or implant of claim 17, wherein said substrate is Ti, a Ti alloy, a stainless steel or a Co—Cr—Mo alloy.

19. A method of surface treatment of at least part of a surface of an insert or implant, said method comprising:
depositing an intermediate bonding layer and an outer coating of a biomaterial on at least part of the surface of the insert or implant such that said intermediate bonding layer is bonded to said substrate and to said outer coating and a mechanical interlock is present between said intermediate bonding layer and said outer coating, wherein said intermediate bonding layer has, in plan, first regions which are relatively thick and second regions which are relatively thin, wherein said first and second regions form, in plan, a substantially regular pattern and wherein the outer coating with intermediate bonding layer is able to support cellular attachment, wherein adjacent first regions are between 5 μm and 80 μm apart, wherein said intermediate bonding layer comprises $TiO_2$, $ZrO_2$, calcium titanate, a complex salt, $Fe_2O_3$, or a composite of the materials of the substrate and the outer coating, wherein the biomaterial comprises hydroxyapatite, and further wherein said intermediate bonding layer has through holes in it such that said outer coating is in contact with said substrate as well as said intermediate bonding layer.

* * * * *